US012727847B2

(12) United States Patent
Joshi et al.

(10) Patent No.: US 12,727,847 B2
(45) Date of Patent: Sep. 8, 2026

(54) CONTINUOUS BLOOD PRESSURE MEASUREMENT SYSTEM AND METHOD

(71) Applicant: KONINKLIJKE PHILIPS N.V., Eindhoven (NL)

(72) Inventors: Rohan Joshi, Eindhoven (NL); Sergei Y. Shulepov, Eindhoven (NL); Kevin Daniel Seng Hung Lau, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 99 days.

(21) Appl. No.: 18/864,048

(22) PCT Filed: May 1, 2023

(86) PCT No.: PCT/EP2023/061427
§ 371 (c)(1),
(2) Date: Nov. 8, 2024

(87) PCT Pub. No.: WO2023/217565
PCT Pub. Date: Nov. 16, 2023

(65) Prior Publication Data

US 2025/0331804 A1 Oct. 30, 2025

(30) Foreign Application Priority Data

May 9, 2022 (EP) .................................... 22172251

(51) Int. Cl.
*A61B 8/06* (2006.01)
*A61B 8/00* (2006.01)

(52) U.S. Cl.
CPC ................ *A61B 8/06* (2013.01); *A61B 8/488* (2013.01)

(58) Field of Classification Search
CPC ....... A61B 8/06; A61B 8/488; A61B 5/02125; A61B 5/022; A61B 5/029; A61B 8/08; A61B 8/5207; A61B 8/085; A61B 8/0858; A61B 8/0891; A61B 8/4236; A61B 8/04
See application file for complete search history.

(56) References Cited

U.S. PATENT DOCUMENTS 7,125,383 B2 10/2006 Hoctor
9,603,533 B2 * 3/2017 Lading ................. A61B 5/0205
12,564,370 B2 * 3/2026 Joshi ...................... A61B 5/029
(Continued)

FOREIGN PATENT DOCUMENTS

EP 3513717 A1 7/2019
WO WO-2021250234 A2 * 12/2021 ........... A61B 5/1072

OTHER PUBLICATIONS

International Search Report Dated Jul. 14, 2023 for International Appln. No. PCT/EP-2023/061427 Filed May 1, 2023.
(Continued)

*Primary Examiner* — Bo Joseph Peng

(57) ABSTRACT

A system and method for measuring blood pressure makes flow velocity measurements from an artery location and vessel diameter measurements from the same artery location, using an ultrasound system. An arterial wave velocity is obtained from the blood flow velocity and vessel diameter and changes in blood pressure are then tracked. A continuous blood pressure estimate is made from intermittent cuff measurements together with tracked changes in blood pressure between those intermittent measurements.

15 Claims, 4 Drawing Sheets

(56) References Cited

U.S. PATENT DOCUMENTS

| | | | | |
|---|---|---|---|---|
| 2002/0055680 | A1* | 5/2002 | Miele | A61B 8/04 600/450 |
| 2002/0173693 | A1* | 11/2002 | Landesberg | A61M 60/441 600/16 |
| 2004/0059234 | A1* | 3/2004 | Martin | A61B 5/024 600/500 |
| 2005/0143640 | A1 | 6/2005 | Hoctor | |
| 2006/0211942 | A1* | 9/2006 | Hoctor | A61B 5/02125 600/485 |
| 2008/0177131 | A1* | 7/2008 | Dancu | G09B 23/28 600/36 |
| 2010/0106016 | A1 | 4/2010 | Orbay | |
| 2013/0178736 | A1* | 7/2013 | Pahlevan | A61B 5/021 600/430 |
| 2015/0230774 | A1 | 8/2015 | Thai | |
| 2017/0181643 | A1* | 6/2017 | Pahlevan | A61B 5/0507 |
| 2017/0281018 | A1* | 10/2017 | Kramer | A61B 5/02007 |

OTHER PUBLICATIONS

Feng J et al: "Determination of Wave Speed and Wave Separation inthe Arterites Using Diameter and Velocity", Journal of Biomechanics, Pergamon Press, NY. vol, 43, No. 3 Feb. 10, 2010, pp. 455-462.

V. Sheshadri, A. Tiwari, M. Nagappa, and L. Venkatraghavan, "Accuracy in blood pressure monitoring: The effect of noninvasive blood pressure cuff inflation on intra-arterial blood pressure values," Anesth. Essays Res., vol. 11, No. 1, p. 169, 2017, doi: 10.4103/0259-1162.181430.

* cited by examiner

CONTINUOUS BLOOD PRESSURE MEASUREMENT SYSTEM AND METHOD

CROSS-REFERENCE TO PRIOR APPLICATIONS

This application is the U.S. National Phase application under 35 U.S.C. § 371 of International Application No. PCT/EP2023/061427, filed on May 1, 2023, which claims the benefit of International application Ser. No. 22/172,251.5 filed on May 9, 2022. These applications are hereby incorporated by reference herein.

FIELD OF THE INVENTION

This invention relates to a method and a computer program of measuring blood pressure, a blood pressure analysis system, and a blood pressure measurement system, and in particular it relates to continuous but non-invasive blood pressure measurement.

BACKGROUND OF THE INVENTION

Continuous blood pressure (BP) monitoring is an important aspect of patient management in perioperative settings. Continuous BP can only be acquired invasively using arterial lines. However, it brings with it risks, such as a risk of nosocomial infections. Furthermore, there is a drive to shorten the period during which invasive BP monitoring is employed. The major barrier to this drive is that there are no suitable alternatives for the continuous assessment of BP.

An alternative to arterial lines is the inflatable pressure cuff. However, a pressure cuff can only provide a measurement at intermittent time periods, for example following a pre-programmed time interval that is set by the clinician, for instance after every 5 or 10 minutes. In such an approach, dynamic changes occurring in BP may be missed between such measurements.

For many perioperative situations, such as assessments of hemodynamic instability, and identifying and differentiating types of shock, continuous BP monitoring is essential.

US 2005/0143640 discloses a system which uses ultrasound data to provide a blood pressure estimation, in combination with a pressure measurement from an inflatable pressure cuff. The ultrasound is used to analyze the propagating waveform at a plurality of locations along the artery and derive the pulsed wave velocity. This is used to derive a blood pressure measurement.

US 2010/0106016 also describes non-invasive continuous blood pressure measurement by combining blood pressure cuff measurements with ultrasound analysis, for monitoring the size, shape and behavior of the artery. This artery information is used to create a mechanical model of the artery from which a blood pressure may be estimated.

These approaches are complex to implement and/or inaccurate. There remains a need for a simple and accurate way to monitor blood pressure continuously and non-invasively.

US 2006/211942 discloses the use of ultrasound to determine a blood flow rate and vessel diameter. A transmission line model is used to relate blood vessel measurements with electrical components. The method uses two sensors or sensor arrays to obtain two different measurements.

SUMMARY OF THE INVENTION

The invention is defined by the independent claims. Dependent claims define advantageous embodiments.

According to examples in accordance with an aspect of the invention, there is provided a method of measuring blood pressure, the method comprising:

- receiving ultrasound blood flow velocity measurements from an artery location; and
- receiving ultrasound vessel diameter measurements from the same artery location using the same, single ultrasound system;
- determining an arterial wave velocity from a diameter-velocity loop relating the blood flow velocity and the vessel diameter;
- tracking changes in blood pressure based on the arterial wave velocity and the blood flow velocity measurements;
- obtaining an intermittently measured blood pressure from a cuff; and
- deriving a continuous blood pressure estimate from the intermittent measurements and the tracked changes in blood pressure between those intermittent measurements.

This method uses ultrasound to continuously obtain velocity and diameter measurements from an arterial location and translate this information to track relative changes in blood pressure. The ultrasound information may be obtained from a wearable ultrasound system. By incorporating information from a blood pressure cuff, the absolute pressure can be tracked continuously. The analysis can be performed by means of closed loop calculations that can be used in real time.

The method may comprise:

- receiving pulsed wave Doppler ultrasound blood flow velocity measurements from the artery location; and
- receiving B-mode ultrasound vessel diameter measurements from the same artery location.

M-mode ultrasound may instead be used for deriving vessel diameter measurements.

A single ultrasound system at a single artery location may thus be used.

The method may comprise obtaining the arterial wave velocity from the rate of change of blood flow velocity with respect to a logarithm of the diameter. The derivative relationship between the blood flow velocity and the diameter yields the arterial wave velocity.

The method may comprise setting the timing of a next cuff measurement based on a level of change of the arterial wave velocity. In this way, the number of cuff measurements can be reduced, saving power and discomfort, when they are not needed. A cuff measurement will not be needed when it can be established that the blood pressure has not changed significantly.

The method may comprise identifying a change in arterial wave velocity that is a predetermined factor more than a threshold level of hemodynamic change. The threshold level for example relates to blood pressure changes due to respiration or due to the action of taking a cuff pressure measurement.

The method may further comprise estimating cardiac output from the blood flow velocity measurement and vessel diameter measurement. Thus, it is possible to continuously and non-invasively track both BP and cardiac output.

The invention also provides a blood pressure analysis system, comprising:

- a single ultrasound system; and
- a processor, wherein the processor is configured to:
  - receive blood flow velocity measurements from an artery location taken by the ultrasound system;

receive vessel diameter measurements from the same artery location taken by the ultrasound system;

determine an arterial wave velocity from a diameter-velocity loop relating the blood flow velocity and the vessel diameter;

track changes in blood pressure based on the arterial wave velocity and the blood flow velocity measurements;

receive an intermittently measured blood pressure from a cuff; and derive a continuous blood pressure estimate from the intermittent measurements and the tracked changes in blood pressure between those intermittent measurements.

This analysis system comprises a processor to perform the method defined above.

The processor is for example configured to set the timing of a next cuff measurement based on a level of change of the arterial wave velocity. It is also, for example, configured to identify a change in arterial wave velocity that is a predetermined factor more than a threshold level of hemodynamic change. It may also estimate a cardiac output from the blood flow velocity measurement and vessel diameter measurement.

The invention also provides a blood pressure measurement system, comprising:

a single ultrasound system configured to:

obtain blood flow velocity measurements from an artery location; and obtain vessel diameter measurements from the same artery location;

a blood pressure measurement cuff; and the blood pressure analysis system defined above.

The ultrasound system for example comprises an ultrasound patch. This provides a comfortable wearable system for continuous blood pressure monitoring.

The ultrasound system of the blood pressure measurement system is for example configured to:

obtain the arterial diameter measurements by B-mode ultrasound imaging; and obtain the blood flow velocity measurements by pulsed wave Doppler ultrasound.

The invention also provides a computer program product comprising a computer program which is configured, when said program is run on the processor of the blood pressure analysis system defined above to perform the method defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
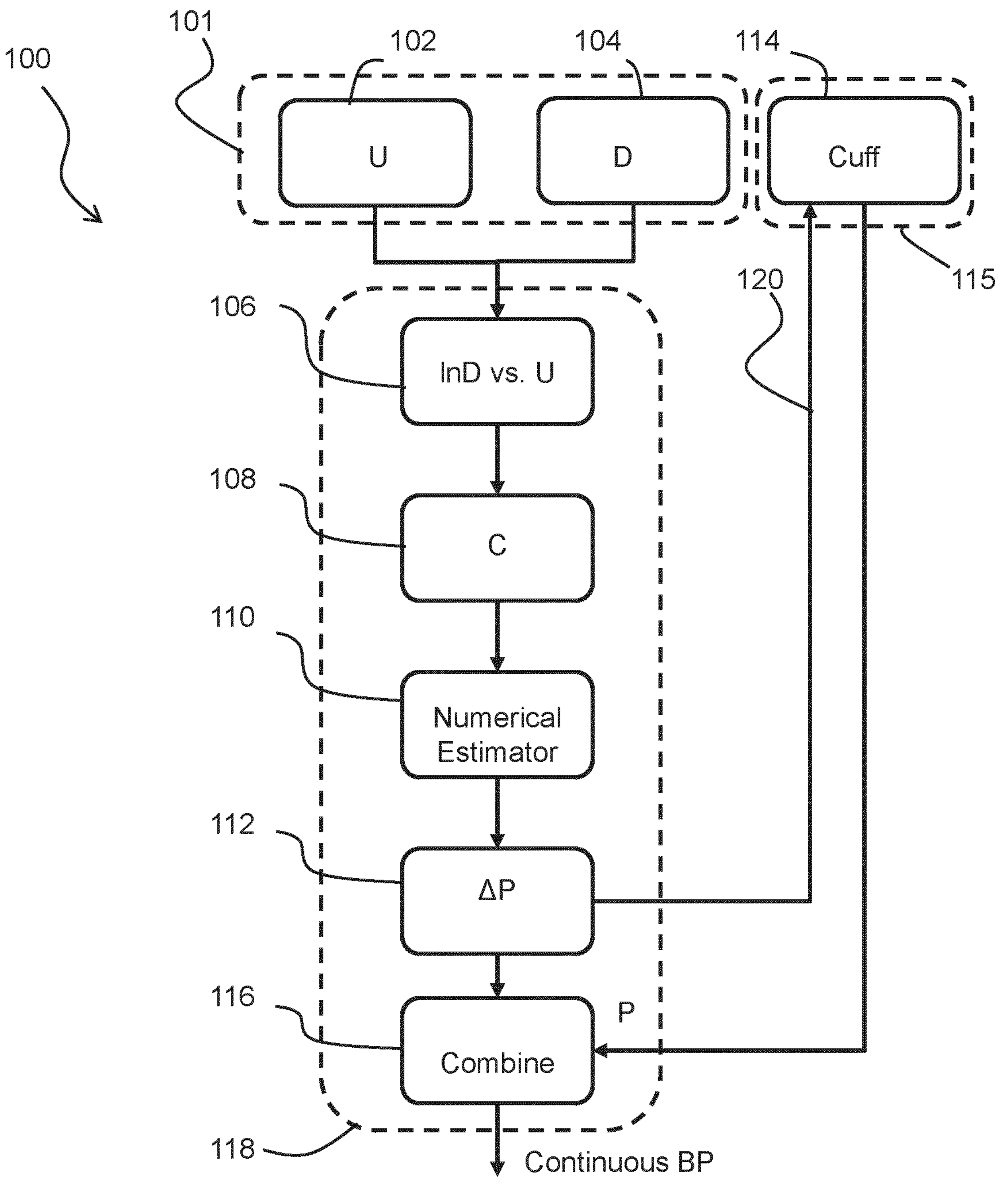
FIG. 1 shows a method and system for measuring blood pressure.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a system and method for measuring blood pressure. The system makes flow velocity measurements from an artery location and vessel diameter measurements from the same artery location, using an ultrasound system. An arterial wave velocity is obtained from the blood flow velocity and vessel diameter measurements and changes in blood pressure are then tracked. A continuous blood pressure estimate is made from intermittent cuff measurements together with tracked changes in blood pressure between those intermittent measurements.

FIG. 1 shows method 100 of measuring blood pressure. The hardware components for performing the method steps are shown as dotted boxes.

An ultrasound blood flow velocity U measurement is obtained in step 102 from an artery location. An ultrasound vessel diameter D measurement is obtained in step 104 from the same artery location. The ultrasound measurements are obtained by an ultrasound system 101.

In step 106, the relationship between the logarithm of the vessel diameter (i.e. lnD) and the blood flow velocity, U, is analyzed.

This enables the arterial wave velocity C to be determined in step 108.

A numerical estimator is used in step 110 to solve equations (explained further below) which link the vessel diameter D, flow velocity U, arterial wave velocity C and pressure. This enables changes in blood pressure to be tracked in step 112, based on preceding arterial wave velocity and the blood flow velocity measurements.

An intermittently measured blood pressure is received from a cuff 115 in step 114. In step 116, a continuous blood pressure estimate is derived from the intermittent measurements and the tracked changes in blood pressure between those intermittent measurements.

The steps 106, 108, 110, 112 and 116 are performed by a processor 118, which processes the received ultrasound data (pulsed mode Doppler ultrasound blood flow velocity measurements and B-mode ultrasound vessel diameter measurements) and the received cuff pressure measurement and derives the continuous BP value.

The core of the invention is thus to use velocity and diameter measurements in an artery using ultrasound to calculate arterial wave velocity, C, and thereafter use C (in conjunction with the blood velocity measurements) to track changes in blood pressure. In combination with a BP that is measured intermittently by using a cuff, the BP can be estimated continuously and non-invasively.

The velocity and diameter measurements may be obtained using an ultrasound patch, and the cuff measurements are obtained using a standard blood pressure cuff. The method can operate in real time.

A wearable ultrasound patch may for example be applied at the carotid to continuously acquire the arterial diameter D via B-mode ultrasound imaging, and local blood velocity U measurements via pulsed wave Doppler (PWD). These D and U measurements can be used to assess the arterial wave velocity C as follows:

$$C = \pm \frac{1}{2} \frac{dU_\pm}{d\ln D_\pm} \quad \text{(Eq. 1)}$$

Figure 2:
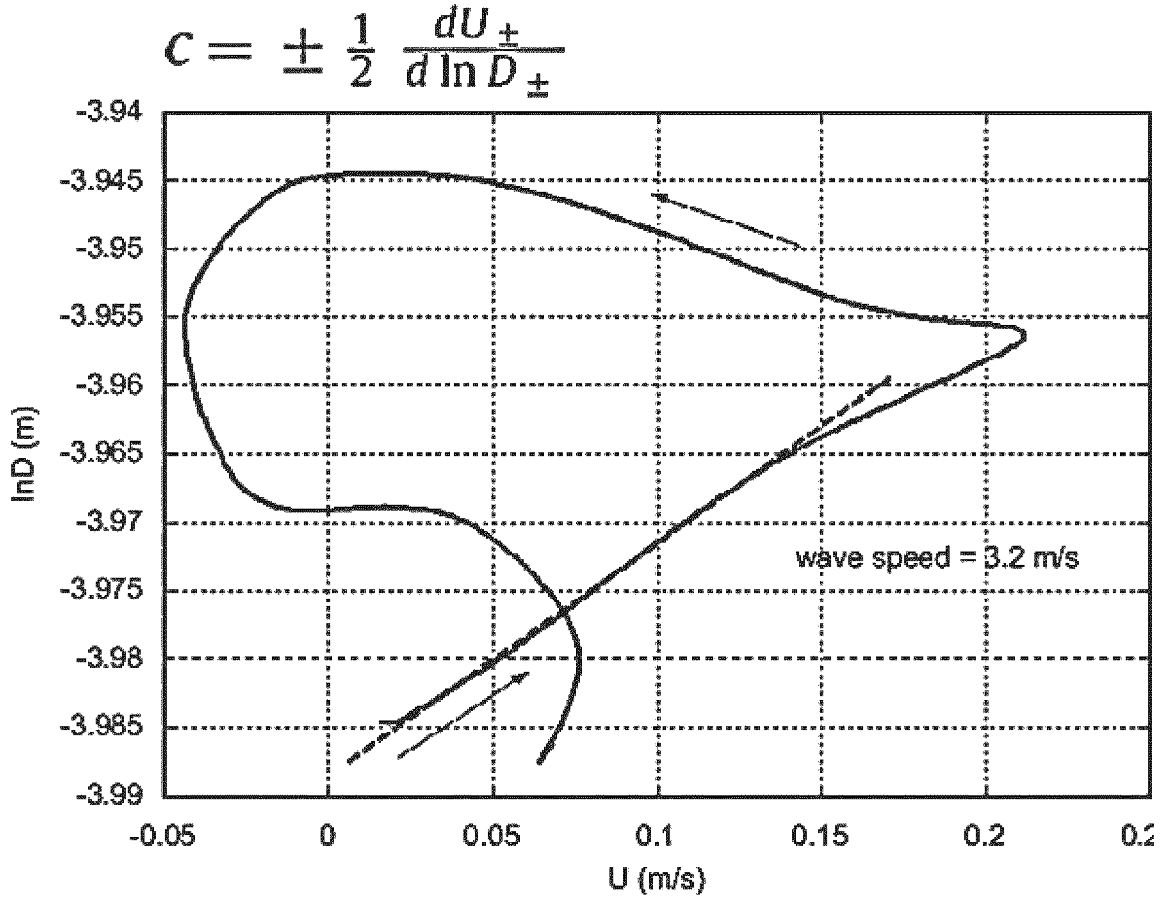
FIG. 2 shows a plot of the natural logarithm of the vessel diameter, i.e. lnD, versus the blood velocity U.

FIG. 2 shows a plot of the natural logarithm of the vessel diameter, i.e. lnD, versus the blood velocity U. The relationship forms a loop during each heartbeat cycle. The diameter-velocity loop relates the blood flow velocity and the vessel diameter (in particular the logarithm of the vessel diameter in this example).

The start and end of each heartbeat at the location where the patch is applied on the artery can be determined from identifying the systolic foot and end diastole from either or both of the D and U waveforms.

Figure 3:
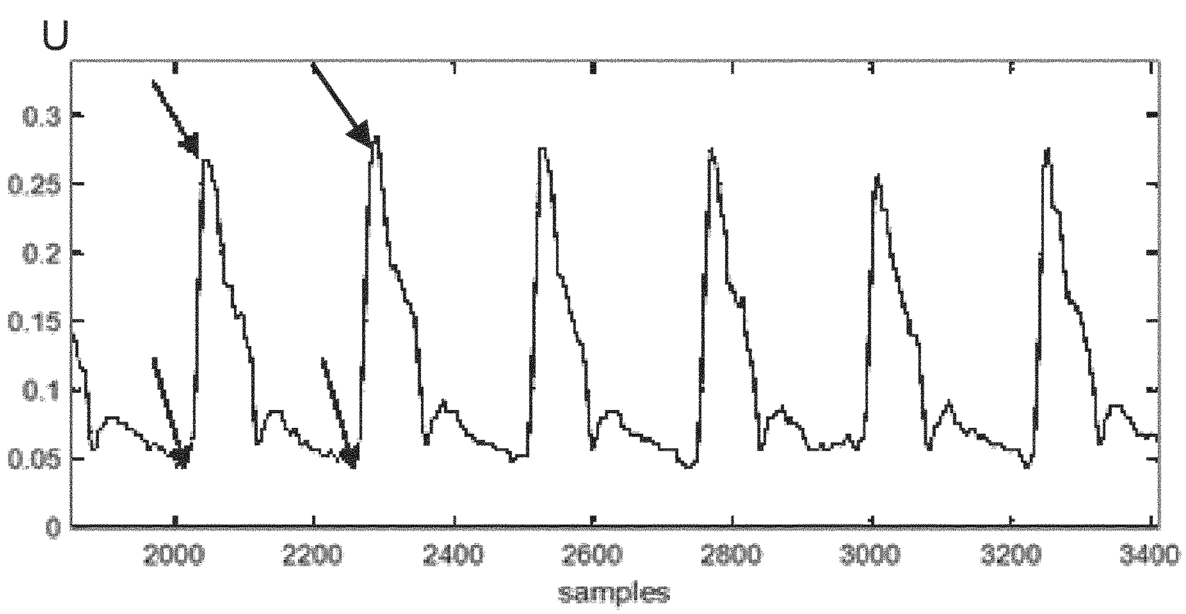
FIG. 3 shows a velocity waveform over time, and shows the systolic foot and end diastole.

By way of example, FIG. 3 shows the velocity waveform over time, and shows the systolic foot and end diastole for the first two pulses.

The change in velocity (dU) can be written as the sum of positive ($dU_+$) and negative velocity ($dU_-$). The positive and negative velocities refer to the forward and backward velocity components of the travelling waves.

A similar interpretation applies for diameter D.

Eq. 1 above describes a linear relationship between U and lnD for unidirectional waves. Since during the early part of systole, reflected waves are unlikely or their effect is minimal, by fitting a straight line to the lnD vs. U loop as shown in FIG. 2, ½ C is obtained and thus C can be derived.

The tangent in the initial part of the loop, e.g., at a location corresponding to before or around the peak systolic velocity, is thus used to yield the arterial wave velocity C. From a computational standpoint, C can be calculated by using the ensemble averaged lnD vs. U loop acquired over multiple heartbeats (i.e., by averaging multiple lnD vs. U loops) or equivalently, C can be calculated per heartbeat and then its average can be taken. When using multiple beats, a quality check can be included, for instance, D and U values from each of the individual beats should remain within a certain range such as two standard deviations or less.

For further explanation reference is made to J Feng. et. al., "Determination of wave speed and wave separation in the arteries using diameter and velocity", J. Biomech. 2010 Feb. 10, 43 (3): pp. 455-462.

As described in this article, when only unidirectional waves are present, this relationship results in a straight line in the early part of the cycle when it is most probable that waves are running in the forward direction. Using the knowledge of wave speed, a set of equations is derived to separate the forward and backward waves from the measured D and U waveforms. Once the forward and backward waveforms of D and U are established, the energy carried by the forward and backward waves is determined.

There is a similar relationship between pressure, arterial wave velocity and the blood flow velocity:

$$C = \pm \frac{1}{\rho} \frac{dP_\pm}{dU_\pm} \quad \text{(Eq. 2)}$$

Figure 4:
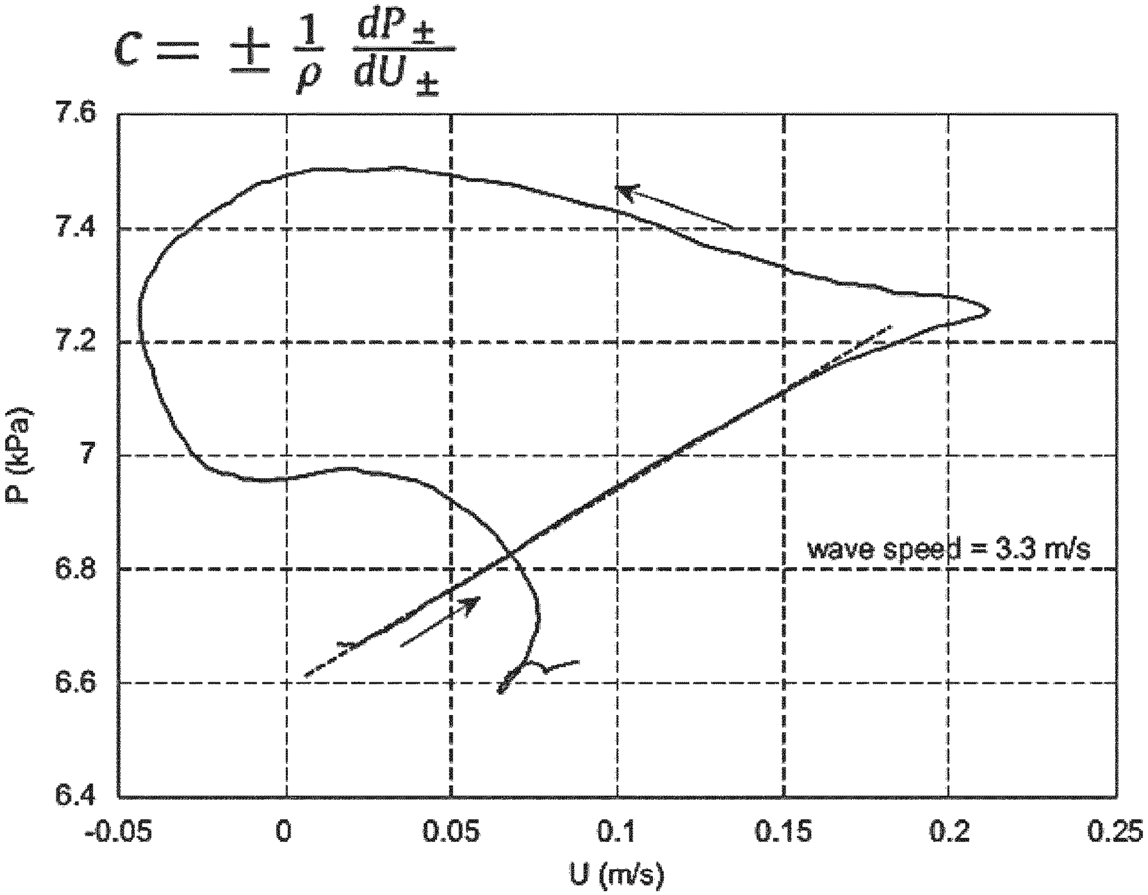
FIG. 4 shows the relationship of pressure P versus blood flow velocity U.

FIG. 4 shows the relationship of pressure P versus blood flow velocity U. Again, the relationship forms a loop for each heartbeat cycle.

Since C and $dU_\pm$ are known and ρ is blood density (a constant), changes in pressure P can be estimated after each heartbeat or after obtaining an average of a set of heartbeats.

The value of C has been calculated from Eq. 1 and the changes in velocity $dU_\pm$ are obtained through the ultrasound measurements. Thus, Eq. 2 can be rearranged to calculate changes in pressure, i.e., ΔP.

The approach outlined above is effective in tracking changes in blood pressure. In conjunction with the intermittent measurements of blood pressure P using the cuff, it becomes possible to track absolute pressure, P+ΔP non-invasively and continuously.

The invention thus enables the use of ultrasound to measure BP by using a single sensor and by taking measurements at a single location, using equations 1 and 2. The simplicity of the equations means that the BP measurement can be implemented in real time, and using an ultrasound sensor that can be placed at a location different (and possible also far) from the cuff location. For example, the ultrasound sensor may be placed at the carotid or femoral artery (or both) while the cuff is placed on one of the arms.

As explained above, using only cuff measurements means dynamic changes occurring in BP may be missed between such measurements. In addition, if the BP remains stable, a new BP cuff measurement is redundant, but making the measurement causes discomfort to the patient. Obtaining cuff-based BP measurements at a predetermined frequency is thus associated with two disadvantages:

(i) BP is a dynamic signal and obtaining only intermittent point measurements can lead to missed clinical insights, especially on trending information. For instance, a patient who has intermittent hypotension may show two normal, consecutive BP measurements with hypotensive episodes occurring in between. Such a scenario can lead to false clinical confidence in the BP stability of the patient.

(ii) Cuff inflation is uncomfortable for patients and can disturb sleep and recovery, for instance.

An optional additional feature is for the cuff-inflation to be dynamically triggered so that it takes place only when there is confidence that the underlying BP has changed from the last cuff measurement by a meaningful extent.

Such a dynamic approach to triggering cuff-based measurements will not only provide richer data and more insights into the BP stability of the patient but also lead to better patient experience owing to improved comfort.

Thus, ultrasound analysis as explained above may be used to non-invasively and continuously assess that the underlying BP has changed by a significant amount from the last cuff-based measurement and may use this information to trigger cuff re-inflation and a new BP measurement. Thus, the changes in pressure may be used to change the timing of the cuff-based measurements.

This is represented in FIG. 1 by the arrow 120.

Eq. 2 above shows that a significant change in arterial wave velocity C is likely to be associated with a significant change in pressure, P. Thus, by quantifying significant changes in C it can be determined when cuff measurements should be taken.

It is known from literature that a cuff inflation can lead to a clinically insignificant increase in BP (e.g., <10 mm Hg). Similarly, respiratory modulation of BP is a well-known phenomenon. These changes in BP will be associated with a change in C.

By exploiting these routinely accessible changes in C, the level at which a change in C is significant can be determined. For example, a change in C may be determined as significant when it differs by a predetermined factor from the normal hemodynamic changes due to respiration or changes incited due to blood pressure cuff inflation. In this manner, a significant change in C can be ascertained, which would reflect a significant underlying change in BP. This determination can then be used to (re-)trigger the BP cuff to obtain a new BP measurement.

There are various approaches for determining what constitutes a meaningful change in C, thereby to mandate new BP measurements.

A first approach is to use a few heartbeats and average their lnD vs. U curves to calculate the ensemble average value of $C_{avg}$ before a cuff inflation. A new value of C is calculated during cuff inflation $C_{cuff}$. The cuff inflation changes BP and thereby also C but only by a clinically insignificant value (<10 mm Hg) as mentioned above.

This is for example reported in V. Sheshadri et. al., "Accuracy in blood pressure monitoring: The effect of noninvasive blood pressure cuff inflation on intra-arterial blood pressure values," Anesth. Essays Res., vol. 11, no. 1, p. 169, 2017.

A cuff re-inflation can then be triggered whenever the ensemble value $C_{avg}$ differs from $C_{cuff}$ by a predetermined factor, e.g., 10%. Then $C_{cuff}$ is recalculated.

Figure 5:
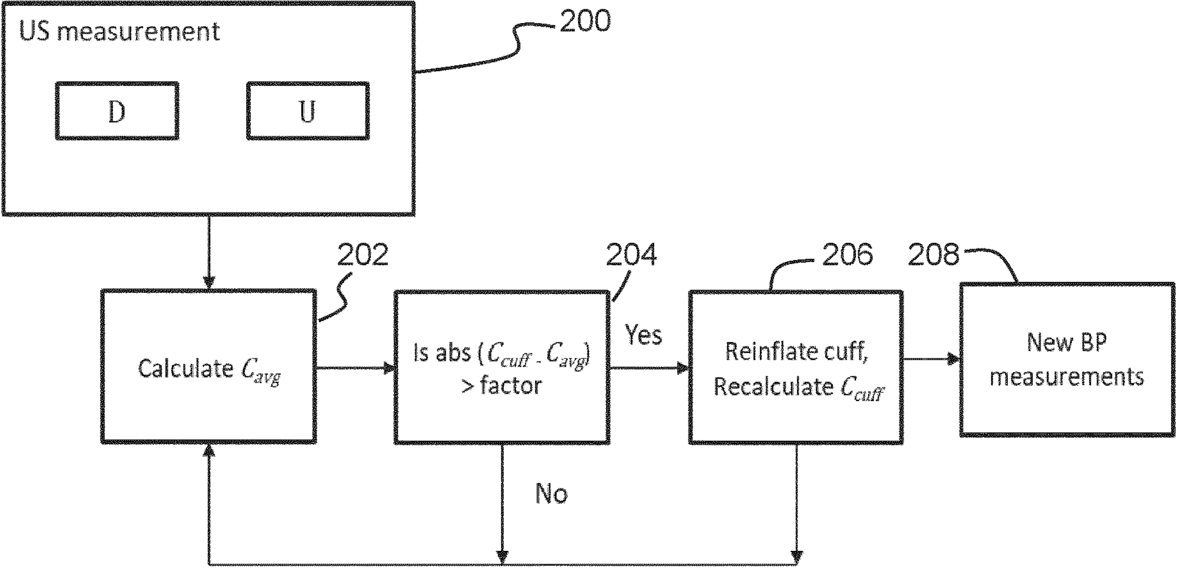
FIG. 5 shows one approach for determining when there is a change in arterial wave velocity to trigger a new cuff measurement.

This approach is shown in FIG. 5.

In step 200, the ultrasound measurements are taken as explained above.

An average arterial wave velocity $C_{avg}$ is calculated in step 202. In step 204, a difference is determined between that average $C_{avg}$ and the arterial wave velocity measurement $C_{cuff}$ during the preceding cuff inflation. If the difference exceeds a threshold, the cuff is re-inflated in step 206 and the new value of $C_{cuff}$ is obtained. The continuous BP measurements continue in step 208.

An alternative, second, approach is to exploit the fact that respiratory modulation also changes BP and thereby the values of C for the heartbeats corresponding to a respiratory cycle. The standard deviation of C, i.e., $C_{resp-sd}$ over one or more respiratory cycles can be calculated. Again, a change in C that is a predetermined factor different to $C_{resp-sd}$ can be used to trigger cuff inflation. After that, $C_{resp-sd}$ can be recalculated.

The slope of the D-U loop may be used for generating a trigger as is clear from the examples above. However, additional triggers may be used such as the area under the curve of the D-U loop, the shape of the D-U loop (i.e., the aspect ratio), etc. These triggers can be generic (e.g., using a defined threshold value) or patient-specific—e.g., a trigger based on exceeding the standard deviations observed in a specific patient, or via contextual information from the patient monitor such as the presence of a ventilator and its settings.

The system may be enhanced with additional functions. One option is to estimate cardiac output.

WO 2021/250234 discloses a method for deriving hemodynamic parameters based on blood velocity and arterial diameter measurements, i.e. the parameters that are obtained by the system and method described above. In particular, stroke volume, stroke volume and cardiac output may be obtained. Thus, it has been shown that velocity and diameter estimations from the carotid can be used to estimate cardiac output (CO). In conjunction with the blood pressure monitoring system described above it is therefore possible to continuously and non-invasively track both BP and CO.

The cuff inflation can affect hemodynamics and CO estimates, so epochs corresponding to cuff inflation should not be used for the CO estimation. The cuff-inflation acts as a triggered event which blocks blood flow by increasing arterial resistance on a limb. The corresponding dilation of the common carotid artery during this time can also be used as a template for the patient if the patient has fluid overload.

The system may also be used for deriving pulse contour or external hemodynamic parameters. Pulse contour analysis requires estimates of arterial compliance and resistance determined from the arterial pressure waveform measured, typically, at a peripheral site. These estimates vary in time, as the patient condition varies. The pulsed wave velocity estimation performed at the carotid can also be used to estimate the (local) arterial compliance. As the anatomical location of the carotid is closer to the central aorta, it is therefore more sensitive to changes in central hemodynamic parameters (e.g. resistance and compliance).

The pulsed wave velocity measurement may thus be used as a trigger to update the hemodynamic parameters of a pulse contour analysis system. Alternatively, variations in a peripheral pressure waveform may be used to trigger the update of carotid pulsed wave velocity.

As explained above, the pulsed wave velocity in the carotid is determined from the initial linear section of the velocity-diameter loop. This is performed on the assumption that the velocity and diameter waveforms are not affected by reflection from peripheral sites (i.e., reflection free). Transition of the linear region to the non-linear region can therefore be used to determine that (increased) reflections are present and therefore vascular tone has changed.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

Functions implemented by a processor may be implemented by a single processor or by multiple separate processing units which may together be considered to constitute a "processor". Such processing units may in some cases be remote from each other and communicate with each other in a wired or wireless manner.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A method of measuring blood pressure, the method comprising:

receiving ultrasound blood flow velocity measurements from an artery location; and receiving ultrasound vessel diameter measurements from the same artery location using the same, single ultrasound system;

determining an arterial wave velocity from a diameter-velocity loop relating a blood flow velocity and a vessel diameter;

tracking changes in blood pressure based on the arterial wave velocity and the blood flow velocity measurements;

obtaining an intermittently measured blood pressure from a cuff; and deriving a continuous blood pressure estimate from the intermittent measurements and the tracked changes in blood pressure between those intermittent measurements.

2. The method of claim 1, comprising:

receiving pulsed wave Doppler ultrasound blood flow velocity measurements from the artery location; and receiving B-mode ultrasound vessel diameter measurements from the same artery location.

3. The method of claim 1, comprising obtaining the arterial wave velocity from the rate of change of blood flow velocity with respect to a logarithm of the diameter.

4. The method of claim 1, comprising setting the timing of a next cuff measurement based on a level of change of the arterial wave velocity.

5. The method of claim 4 comprising identifying a change in arterial wave velocity that is a predetermined factor more than a threshold level of hemodynamic change.

6. The method of claim 1, further comprising estimating cardiac output from the blood flow velocity measurement and vessel diameter measurement.

7. A blood pressure analysis system, comprising:

a single ultrasound system; and a processor, wherein the processor is configured to:

receive blood flow velocity measurements from an artery location taken by the ultrasound system;

receive vessel diameter measurements from the same artery location taken by the ultrasound system;

determine; an arterial wave velocity from a diameter-velocity loop relating a blood flow velocity and a vessel diameter;

track changes in blood pressure based on the arterial wave velocity and the blood flow velocity measurements;

receive an intermittently measured blood pressure from a cuff; and derive a continuous blood pressure estimate from the intermittent measurements and the tracked changes in blood pressure between those intermittent measurements.

8. The blood pressure analysis system of claim 7, wherein the processor is configured to set the timing of a next cuff measurement based on a level of change of the arterial wave velocity.

9. The blood pressure analysis system of claim 8, wherein the processor is configured to identify a change in arterial wave velocity that is a predetermined factor more than a threshold level of hemodynamic change.

10. The blood pressure analysis system of claim 7, wherein the processor is configured to estimate a cardiac output from a blood flow velocity measurement and a vessel diameter measurement.

11. The blood pressure analysis system of claim 7, wherein the processor is configured to obtain the arterial wave velocity from the rate of change of blood flow velocity with respect to a logarithm of the diameter.

12. A blood pressure measurement system, comprising:

a blood pressure measurement cuff; and a blood pressure analysis system comprising:

a single ultrasound system configured to:

obtain blood flow velocity measurements from an artery location; and obtain vessel diameter measurements from the same artery location; and a processor, wherein the processor is configured to:

receive the blood flow velocity measurements from the artery location taken by the single ultrasound system;

receive the vessel diameter measurements from the same artery location taken by the single ultrasound system;

determine an arterial wave velocity from a diameter-velocity loop relating a blood flow velocity and a vessel diameter;

track changes in blood pressure based on the arterial wave velocity and the blood flow velocity measurements;

receive an intermittently measured blood pressure from the blood pressure measurement cuff; and derive a continuous blood pressure estimate from the intermittent measurements and the tracked changes in blood pressure between those intermittent measurements.

13. The blood pressure measurement system of claim 12, wherein the ultrasound system comprises an ultrasound patch.

14. The blood pressure measurement system of claim 12, wherein the ultrasound system is configured to:

obtain the vessel diameter measurements by B-mode ultrasound imaging; and obtain the blood flow velocity measurements by pulsed wave Doppler ultrasound.

15. A non-transitory computer-readable medium that stores therein a computer program product, which, when executed on a processor, causes the processor to perform the method of claim 1.

* * * * *